United States Patent [19]
Patel et al.

[11] Patent Number: 5,803,334
[45] Date of Patent: Sep. 8, 1998

[54] ULTRASONIC EDGE SENSOR FOR THE DETECTION OF A WEB EDGE

[75] Inventors: Arvind Ishwarial Patel, Unjha - Gujarat, India; Gerhard Alt, Kleinaitingen, Germany; Wolfgang Krauth, Friedberg-Wulfertshausen, Germany; Hans Seibold, Anhausen, Germany

[73] Assignee: Erhardt + Leimer GmbH, Augsberg, Germany

[21] Appl. No.: 583,231

[22] Filed: Jan. 5, 1996

[30] Foreign Application Priority Data

Jan. 13, 1995 [DE] Germany .......................... 195 00 822.7

[51] Int. Cl.[6] .......................... B23Q 15/00; B65H 26/00
[52] U.S. Cl. .............................................................. 226/45
[58] Field of Search ........................................ 226/15, 45

[56] References Cited

U.S. PATENT DOCUMENTS

| | | | |
|---|---|---|---|
| 3,570,624 | 3/1971 | O'Connor | 226/45 |
| 5,027,993 | 7/1991 | Ferguson | 226/45 |
| 5,072,414 | 12/1991 | Buisker . | |
| 5,274,573 | 12/1993 | Buisker . | |

*Primary Examiner*—Daniel P. Stodola
*Assistant Examiner*—Matthew A. Kaness
*Attorney, Agent, or Firm*—Herbert Dubno

[57] ABSTRACT

An edge sensor working on ultrasonic principles is used to protect the edge of a travelling web and has a plurality of sensor units with adjacent or overlapping ultrasonic measurement fields between the transmitter and receiver of each unit. The units are switched so that only one unit serves to output a receiver signal when the edge crosses over into the respective measurement field.

11 Claims, 9 Drawing Sheets

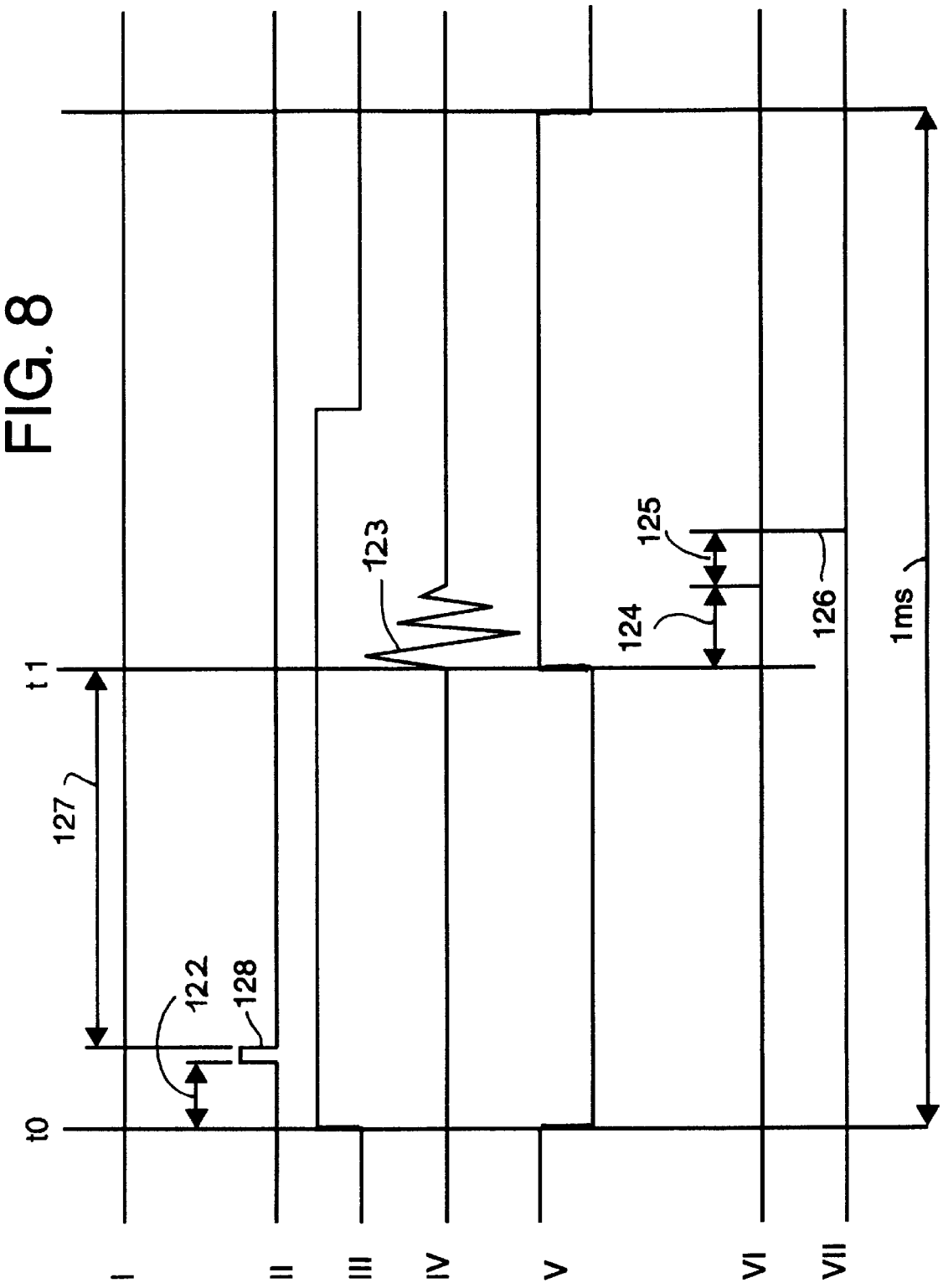

ULTRASONIC EDGE SENSOR FOR THE DETECTION OF A WEB EDGE

FIELD OF THE INVENTION

The present invention relates to an ultrasonic edge sensor for detecting the position of an edge of a web. More particularly, the invention relates to an edge detecting sensor having at least two ultrasonic sensors, each with a sensor transmitter and a sensor receiver and energized with short ultrasonic wave pulses.

BACKGROUND OF THE INVENTION

In the production or treatment of webs of material, e.g. fabric, paper, films, foils and the like, a process line for the web may require detection of the position of the edge of the web in a direction transverse to the web travel direction, i.e. in the width direction. Utilizing the detection of an edge position, the position of the web can be corrected or adjusted by, for example, causing the web to shift to one side or another. Alternatively, control may be provided in the web producing unit to alter the width of the web.

In any case, sensors for detecting the edge of the web can be provided in the form of optical detectors, which are not advantageous when the web is composed of a light sensitive material. Detectors can utilize some other energy source such as, for example, ultrasonic waves.

In a system as described in U.S. Pat. No. 5,072,414, ultrasonic waves are utilized and the device has two ultrasonic edge detecting sensors, only one of which is disposed in the edge region of the web and serves for the actual detection of the position of the edge. The second sensor is located outside the edge region and serves to generate compensating parameters allowing compensation for environmental conditions like air temperature, air humidity, etc. which may affect the received signal of the first sensor and can serve as a basis for normalizing the received signal.

The received signal and the compensation parameters are obtained from the electrical sensor signals by rectification, peak value detection and digitalization. Between the two sensors a switching unit functioning as a multiplexer is provided so that mutual switching effects on the sensor outputs are avoided. The processing of the receiver signals and the compensation parameters to the sensor output signal is effected in a computer and, in particular, by averaging each sequence of receiver signals and compensation values. The ultrasonic wave signals transmitted by the sensors and received by the respective receivers are short acoustic pulses which are as brief as possible and have a frequency of about 200 kHz.

DE 34 42 154 C2 discloses a single edge sensor with only a single ultrasonic sensor which, to avoid perturbation of the measurement signal by echo signals has its sensor receiver activated only during certain time intervals which are later by the expected travel time of the sonic pulses than the initiation of the transmission and which end prior to the arrival of the first echo signals. Here as well the electrical sensor signals are detected utilizing peak value detection techniques. All such edge sensors have the drawback that the measurement field extends in the direction of the width of the web but to a relatively small extent as is especially the case when the dependency of the sensor output on the web edge position should be as linear as possible in the measurement field.

OBJECTS OF THE INVENTION

It is, therefore, the principal object of the present invention to provide an ultrasonic edge sensor in which the measurement range in the width direction can be as large as desired but yet the dependency of the sensor output signal upon the edge position of the web is linear.

Another object of the invention is to provide an improved edge detection system for the purpose described whereby the limitations are avoided and particularly the sensor output is linearized in a simple manner.

It is also an object of the invention to provide an edge sensor system for travelling webs which can overcome drawbacks of earlier systems.

SUMMARY OF THE INVENTION

These objects and others which will become apparent hereinafter are attained, in accordance with the invention with a system for detecting the edge position of a web which comprises at least two ultrasonic sensors each of which has a sensor transmitter which emits short ultrasonic wave pulses, and a sensor receiver which picks up the ultrasonic wave pulses and transduces them into electrical signals representing the ultrasonic wave detected.

Each sensor establishes a respective measurement field which extends continuously from the sensor transmitter to the sensor receiver and is formed by the ultrasonic wave pulses travelling from the transmitter to the receiver and the receiver outputs a sensor signal which is dependent upon the degree of masking or interruption of the measurement field by the web.

A switching device is provided for switching each transmitter and receiver for the respective sensor and for switching among the plurality of sensors. A signal converter is provided for generating a digital receiver signal from the sensor signal outputted by the respective switched on sensor and the signal converters are connected to a computer which calculates the edge position from the respective receiver signals and can be used to control a web guide device or mechanism.

According to the invention, this system is characterized by the following features:

A. The measurement field of each sensor is limited in the web width direction by two imaginary boundary edges at which the receiver signal of the respective sensor is at a maximum of one side of the respective edge of the measurement field and at a minimum at the opposite side of the measurement field. The maximum and minimum values constitute limiting values for the respective measurement field, the sensors being spaced apart so that the measurement fields of a plurality of sensors are arrayed one after the other in the web width direction without any gaps between them.

B. A forward-backward counting counter (up-down counter) is provided with at least a number of possible counter stages corresponding to the number of sensors, with the sensors in the sequence of their measurement fields corresponding to the sequence of the counter-states and the counter of the switching unit for the sensors is so controlled that the respective counterstate is switched on for each switched on sensor.

C. A comparator circuit is provided for an actual edge position of the web, a respective value of the receiver signal is generated which is compared with the boundary edge positions of the switched on sensors and upon exceeding the maximum or under shooting the minimum limiting value, the counter is forward stepped or backward stepped to the counter state in which, for the next sensor the actual edge position will lie between the limiting values.

D. A calibration data storage is provided in which the receiver signal is stored as a function of the switched on sensor and in which calibration values for the sensor output signals are stored for the calibration edge positions which are selected for calibration and are distributed over all of the measurement fields.

E. The computer calculates for the receiver signal of an actual edge position the actual value of the sensor output from the stored calibration values for the switched on sensor.

It will be apparent that with the invention in the case of a number of sensors with measurement fields which are achieved one another in the width direction, the sensors of the row are switched on one after another, i.e. sequentially so that the measurement ranges collectively from a wide range in the width direction with an overall width corresponding to the number of sensors.

As a consequence, where a broadening of the range is desired, any number of sensors can be provided. However, since only one of the sensors is activated at any time and produces the output which is utilized to determine the actual position of the web edge, the sensors do not transfer with one another and the measurements can be taken at a high repetition rate although only a single sensor operates at any time. An important further advantage of the invention is that the measurement fields themselves can have limited widths so that the dependency of the actual receiver signal upon the actual or true edge position can have a characteristic which is largely linear between the boundary edge conditions. The measurement sensitivity does not change significantly for each sensor and since only one sensor operates at any time, over the entire range of measurement. Every actual value of a receiver signal for the given operative sensor will lie within the range between calibration values stored for that sensor, in the simplest case of linear interpretation can be made and by the choice of the calibration values, the dependency of the sensor output signal upon the receiver signal and thus the characteristic of the sensor can be highly linearized without requiring an excess number of sensors for a sufficient measurement range. The calibration values can be produced by inserting a calibration diaphragm or shutter to predetermined edge positions within the head to simulate the web, the respective measured receiver signals and the sensor output signals which correspond to these edge positions being stored as calibration values. The calibration boundaries are then determined to yield the desired degree of linearity.

It is also possible to provide the measurement fields of the sensors so that only the boundary edges coincide. In this case, there is a danger that the comparator circuit which controls the sensors via the counter will operate unreliably at these boundary edges. A repeated back and forth switching between the sensors can result when the received signal differs only slightly in the regions of the limiting values. The result can be difficulties in processing the received signal since the acoustic signals from different sensors may be combined. The switching hysteresis is of assistance here. It has been found to be advantageous to provide successive measuring fields so that they overlap at least pairwise. At least the boundary edge regions of each sensor can have calibration positions and thus associated calibration values which are equal to the limiting value serving for sensing switchover so that the limiting values need not be independently stored and reproduced. Nevertheless for each measurement field overlap, two calibration edge positions are required which correspond to the boundary positions and which is a drawback for the calibration process. To avoid this disadvantage and, in accordance with the invention, each overlap region of the measurement fields is characterized by only a single calibration edge position to which two calibration values of the receiver signal are assigned, namely one for each of the two sensors which are active for the overlapping measurement fields and these two calibration values form the comparison values with which the actual receiver signal is compared for the respective switched on sensor. The comparator circuit has a switching hysteresis so that the limiting value differs by the hysteresis value by the calibration value for sensor switching and the maximum boundary value is greater by the hysteresis interval or the minimum boundary value is less by the hysteresis interval than the respective calibration value.

For the hysteresis interval a signal difference of about 1% of the maximum value of the sensor signal will equally suffice. In principal, each boundary value can have a respective comparator unit which compares the receiver signal with this boundary value. This, however, increases the cost of the circuitry for the comparator components which can be twice the number of comparator units than is required here where there is measurement field overlap as has been described.

According to a further feature of the invention, however, this added expense can be avoided by providing the comparator circuit with only two comparator units each having two inputs and one output. A first input of each comparator unit receives the actual receiver signal and the other input a calibration value of the receiver signal from the calibration data storage. The two calibration values are switched to the comparator units in the sequence of switching of the sensors one after another in accordance with the calibration edge positions and the outputs of the two comparators are combined through logic components to advance or reduce the counter when the actual receiver signal is greater than the larger or smaller than the lesser of the two respectively switched calibration values. Advantageously, a further logic unit is provided to combine the comparator outputs and generates a reset signal for the comparator when the actual receiver signal is not an interval between the two respectively switched calibration values.

This insures that the computer will only respond to the calibration value for the receiver signal of a sensor output between the boundary intervals and simplifies the operation of the computer.

According to a further feature of the invention, the counter circuitry includes a first up/down or forward/back counter directly switched by the logic units and a second up/down or forward/back counter which is switched by the first counter. The first counter has a number of counter states corresponding to the number of calibration edge positions for each sensor which are successively met in the measurement field of each sensor while the second counter has a number of states corresponding to the number of sensors. The two counters control, via their counter states an address decoder for the calibration data storage. The counter system thus serves not only for controlling the switchover of the sensors and thus determines the sensor which is active at any point but also controls the corresponding switching of the comparator circuit and the computer to the calibration value stored in the calibration data storage.

Advantageously, each sensor has the same number of calibration edge positions which provides the advantage that the first sensor serves for determining the edge positions for each sensor and need only be reset upon switchover from one sensor to the next. If, on the contrary, the sensors would have different numbers of calibration edge positions, for each of the sensors a respective first counter would have to be provided with the corresponding number of calibration edge positions and counterstates. The outputs of such first counters would have to be combined in logic circuitry so that all of the first counters could be controlled depending upon the state of the second counter.

According to a feature of the invention, for each sensor and each calibration edge position calibration values are stored in the calibration data storage for a proportionality factor which, for each calibration edge positions, gives the relationship between the received signal and the sensor output signal and can provide the actual edge position in terms of the value S for the output signal for the value W of the receiver signal in accordance with the equations $$S = S_{kn} + m_{kn} * (W - W_{kn}).$$

$$m_{kn} = \frac{S_k(n+1) - S_{kn}}{W_{k(n+1)} - W_{kn}}$$

wherein $W_{kn}$, $S_{kn}$ and $W_{k(n+1)}$ and $S_{k(n+1)}$ are the calibration values for the received signal and the sensor output signal $n^{th}$ and $(n+1)^{th}$ calibration edge positions, while $m_{kn}$ is the calibration value the proportionality factor relating the calibration values $W_{kn}$ and $S_{kn}$. This allows the computer to be somewhat simplified since it can simply form the difference $(W_{kn}-W)$ via a subtractor, have a multiplier for forming the product $M_{kn}(W_{kn}-W)$, and can have a summer or adder for forming the sum of $S_{kn}$ and that product. The calibration value $M_{kn}$ of the proportionality factor can be determined by the calibration procedure described above utilizing insertion of the calibration diaphragm and storing the resulting signals and calculating the corresponding value $M_{kn}$. It is also possible, with a corresponding modification of the computer, to calculate the calibration value $M_{kn}$ at each actual measurement procedure anew from the calibration values $W_{kn}$, $S_{kn}$ for each edge position which will be obtained from the counterstate of the counter circuitry.

Simple scattering between the sensors should be compensated to the greatest extent possible. For this purpose the invention provides that, for the transmitter voltage of the sensors, a voltage generator is provided with an adjustable voltage output. For each sensor, therefore, a characteristic calibration voltage at the voltage generator is produced which will insure that the receiver signal for each measurement field in the absence of an edge of a web or a calibration edge, i.e. in the free gap, is the same for all the sensors. The sensors are then switched over to the respective calibration voltages when they are respectively activated.

BRIEF DESCRIPTION OF THE DRAWING

The above and other objects, features, and advantages will become more readily apparent from the following description, reference being made to the accompanying drawing in which:

FIG. 8 is a timing diagram elucidating the measurement sequence for the edge sensor.

SPECIFIC DESCRIPTION

Figure 1:
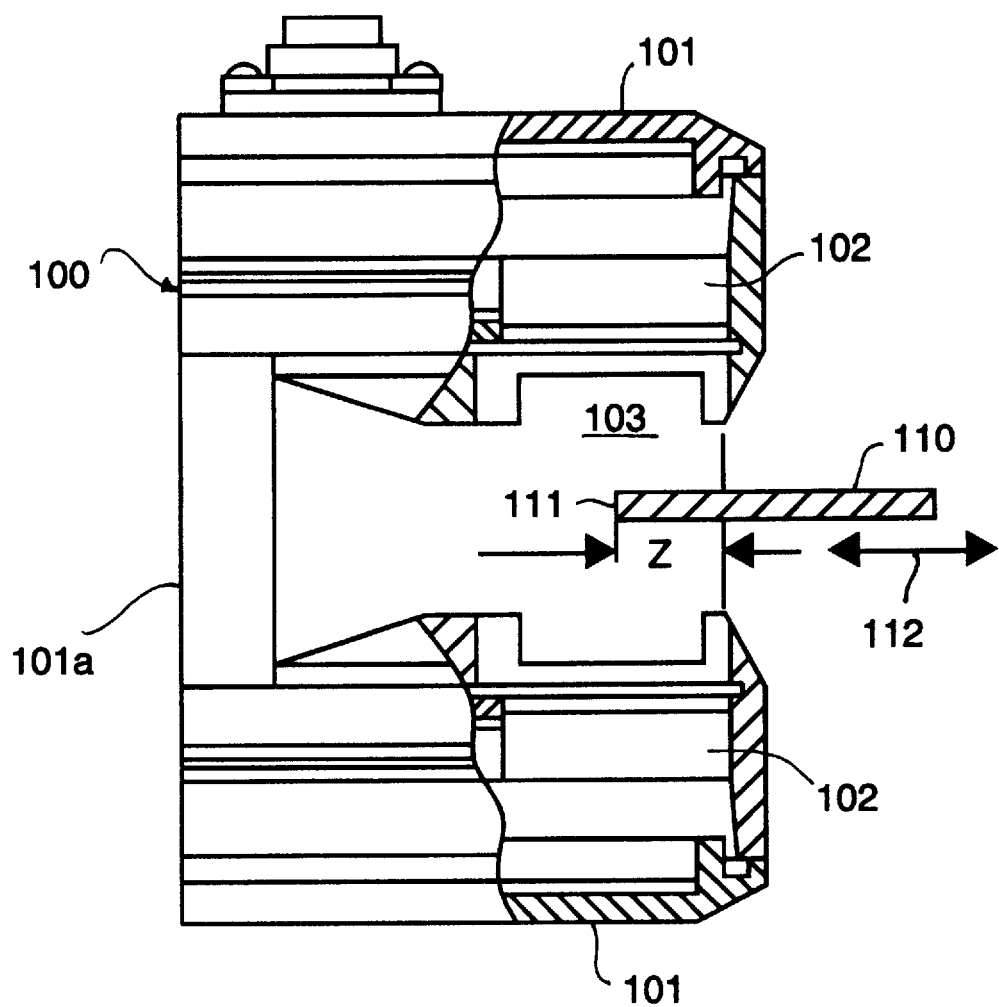
FIG. 1 is a side elevational view of a measurement head utilizing the principles of the invention, taken in the direction of web travel and partly in section.

The ultrasonic edge sensor of the invention comprises, as shown in FIG. 1, a measuring head 100 in the form of a U-shaped stirrup with shanks 101 which straddle the web 110 and a base 101a bridging the shanks 101. On the shanks 101 are ultrasonic oscillators 102 one of which functions as the ultrasonic transmitter while the other functions as the ultrasonic receiver. The two oscillators 102 are juxtaposed with one another across the measurement gap 103 and form between them a sonic path which is traversed by ultrasonic waves on their way from the ultrasonic transmitter to the ultrasonic receiver. The web 110 has its edge 111 extending into the gap 103 and the position of the edge 111 can change in the width direction represented by arrow 112. The ultrasonic waves travelling along the path are thus more or less influenced by the masking effect of the web 110, this phenomenon serving to enable the detection of the edge position.

Figure 2:
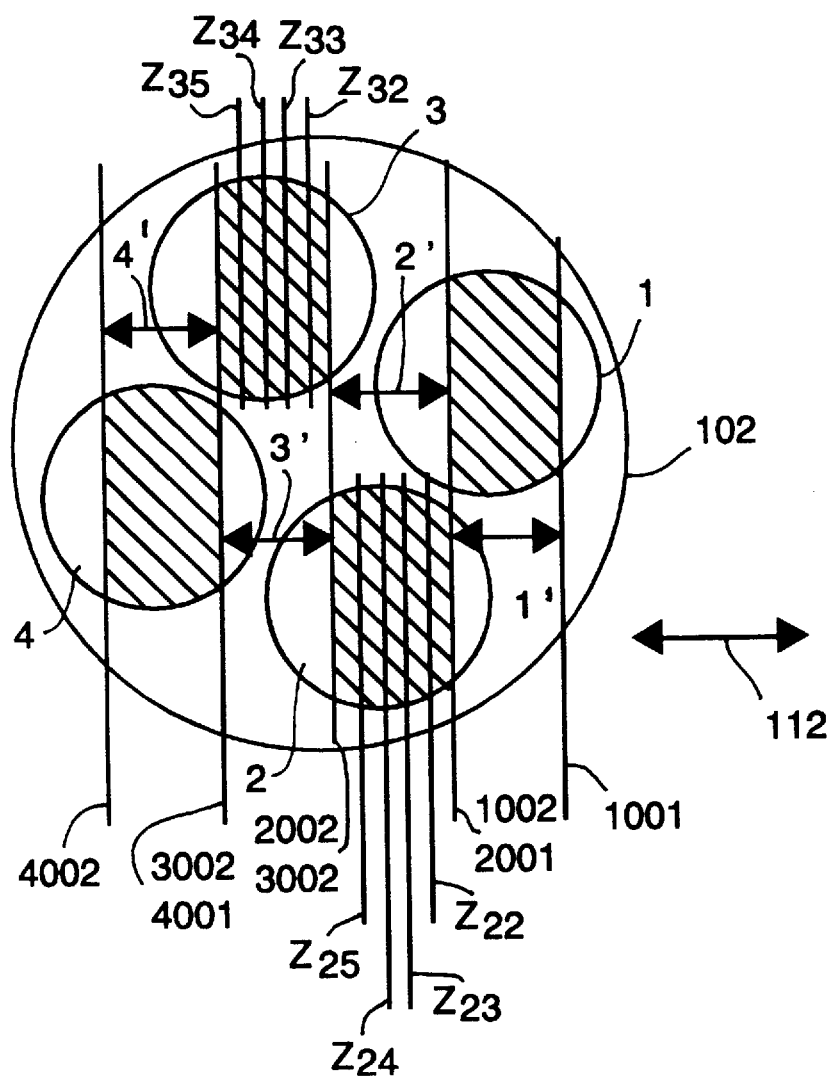
FIG. 2 is a plan view of one of the ultrasonic oscillators of the measuring head of FIG. 1 drawn to a larger scale.

As can be seen from FIG. 2, each acoustic oscillator 102 can comprise a plurality, of circular ultrasonic sensors 1, 2, 3, 4, preferably four in number, which are staggered with respect to the breadth direction 112 and with respect to the longitudinal direction and comprised of respective sensor transmitters 1.1, 2.1, 3.1, 4.1 and respective sensor receivers 1.2, 2.2, 3.2, 4.2. Each sensor receiver 1.2, 2.2, 3.2, 4.2 is juxtaposed with the associated sensor transmitter 1.1, 2.1, 3.1, 4.1 across the gap 103 to form the respective ultrasonic sensor 1, 2, 3, 4 therewith. The staggered arrangement of the sensors has been shown in FIG. 2.

Each sensor creates a respective measurement field 1', 2', 3' 4' in the acoustic path or stretch. These measurement fields have been shown in FIG. 2 by hatching. The outermost sensor 1 in the gap 103 forms the measurement field 1', the next following sensors 2 and 3 form the measurement fields 2' and 3', respectively, and the innermost sensor 4 forms the measurement field 4'.

The sensor transmitter 1.1, 2.1, 3.1, 4.1 for each field (FIG. 4) transmits in each case very short ultrasonic wave pulses.

The associated sensor receivers 1.2, 2.2, 3.2, 4.2 form electrical sensor signals from the ultrasonic wave pulses picked up from the respective measurement fields 1', 2', 3', 4'. These electrical sensor signals vary depending upon the degrees of masking of the measurement fields 1', 2', 3', 4' by the web 110.

A switching unit designated generally at 20 in the drawing and forming a multiplexer, switches each sensor transmitter 1.1, 2.1, 3.1, 4.1 on only with the respective sensor receiver 1.2, 2.2, 3.2, 4.2, the switching of the sensor transmitters 1.1, 2.1, 3.2, 4.1 being effected by the switching portion 20.1 and the switching of the sensor receivers 1.2., 2.2, 3.2, 4.2 being effected by the switching part 20.2. The switching device 20 with the two switching parts 20.1 and 20.2 can switch over between the sensors 1 to 4 in a controlled manner which will be described in detail below.

Figure 4:
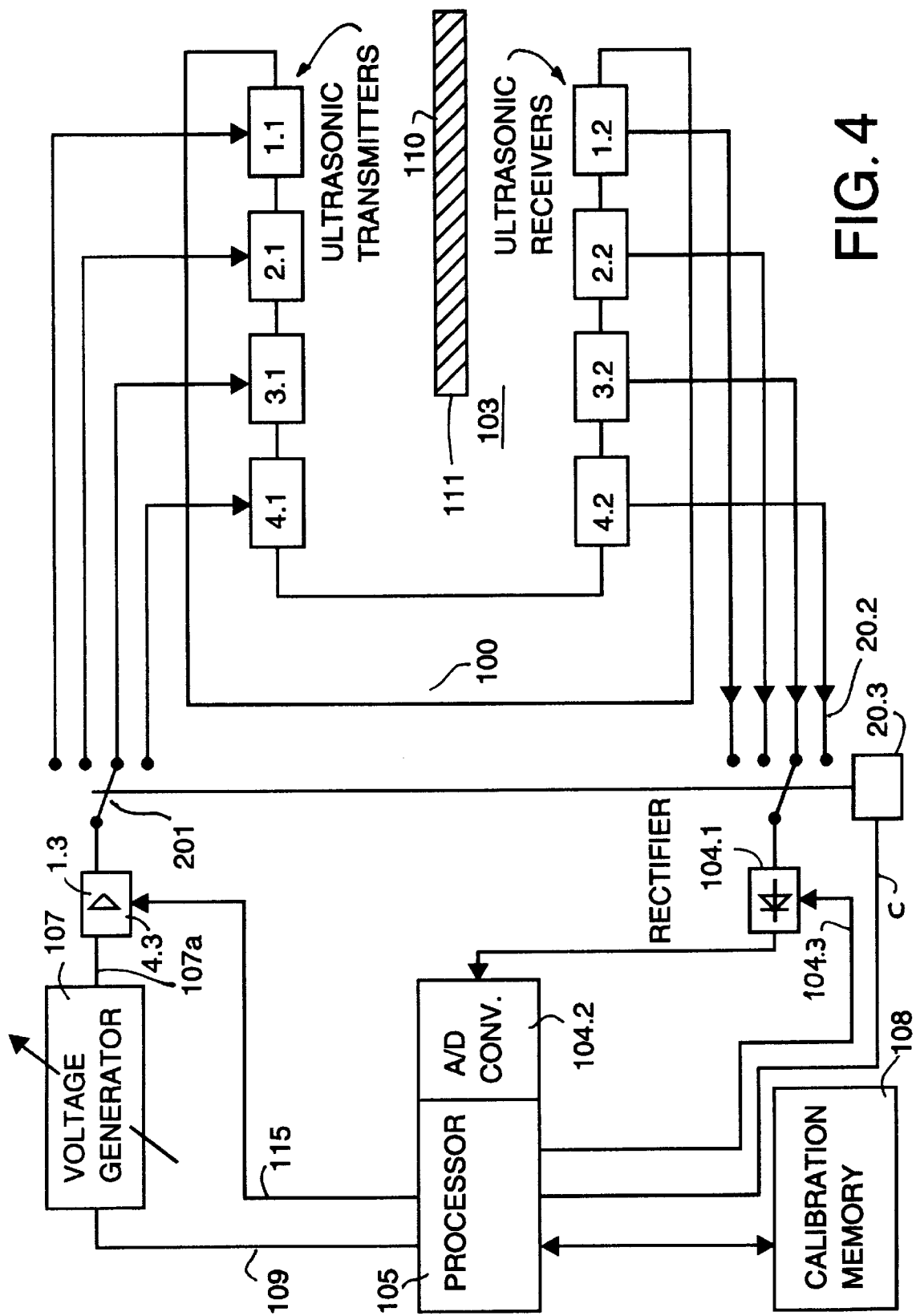
FIG. 4 is a block diagram of the edge sensor in a highly simplified showing.

The electrical sensor signals that are enabled by the switching part 20.2 are processed through a signal converter to yield the received signal W which is initially handled as an analog value and then digitalized. In FIG. 4 the third of the sensor receivers 3.2 has been shown to provide the output while the third of the sensor transmitters 3.1 is correspondingly activated.

In the analog signal processing, a peak value rectifier 104.1 is provided and digitalization is effected of the resulting signal peak by an analog/digital converter 104.2. The peak value rectifier 104.1 can be energized by a processor 105 via line 104.3 so that it operates only for a predetermined time interval from the occurrence of the reception of the ultrasonic wave pulse. The processor 105 (FIG. 4) includes a computer shown in greater detail in FIG. 6 at 106 which generates from the receiver signal W a sensor output signal S representing the edge position and which can be used to control a web guide device controlling the position of the web edge in a feedback loop but not shown here. The edge sensor thus form s a closed control circuit for the edge position of the web.

To compensate for sample scattering by the sensors 1 through 4, a voltage generator 107 is provided for generating the transmitter voltage which can have a variable magnitude and can be adjustable to provide for each sensor 1 through 4, a respective calibration voltage.

The magnitudes of these calibration voltages are such that each sensor 1 through 4 with its respective calibration voltages can produce across the empty gap 103 the same level of the received signal W as the other sensors. In an automatic calibration stage with the completely empty gap 103 the sensors 1 to 4 are sequentially switched on with the switching parts 20.1 and 20.2 of the multiplexing system and the individual transmitter voltages for the respective sensors varied until the identical receiver signals W are obtained at the output of the analog/digital converter 104.2 for each of the sensors.

The so determined calibration voltages for the sensors can be stored in a calibration storage or memory 108 which can dialog with the processor 105.

After calibration, when the system is used to detect the position of the edge between the sensors, via controlled line 109 the voltage generator 107 can be switched so that the requisite voltage is applied to each of the sensors so that each sensor is always operated with its predetermined calibration voltage. While FIG. 4 has a single line 107a supplying all of the sensor transmitters 1.1, 2.1, 3.1, 4.1 with the output from the voltage generator 107, it will be understood that the voltages applied to each transmitter will be the characteristic voltage required for the actual sensor. If another sensor is switched in, the transmitter voltage must be altered to its calibration value. For each sensor transmitter a respective booster 1.3 to 4.3, e.g. a capacitor, can be provided which is charged with the calibration voltage for the respective sensor and then discharged to provide the ultrasonic wave pulse at the transmitter. In practice, the units 1.3 to 4.3 can represent an electronic switch and capacitance system or exclusively an electronic switch such as a thyristor or SCR (see FIG. 7) the trigger signal can be supplied by the processor 105 via line 115 as, for example, a 5 $\mu$s wide pulse 128 (FIG. 8) for the respective booster 1.3 to 4.3.

Figure 5:
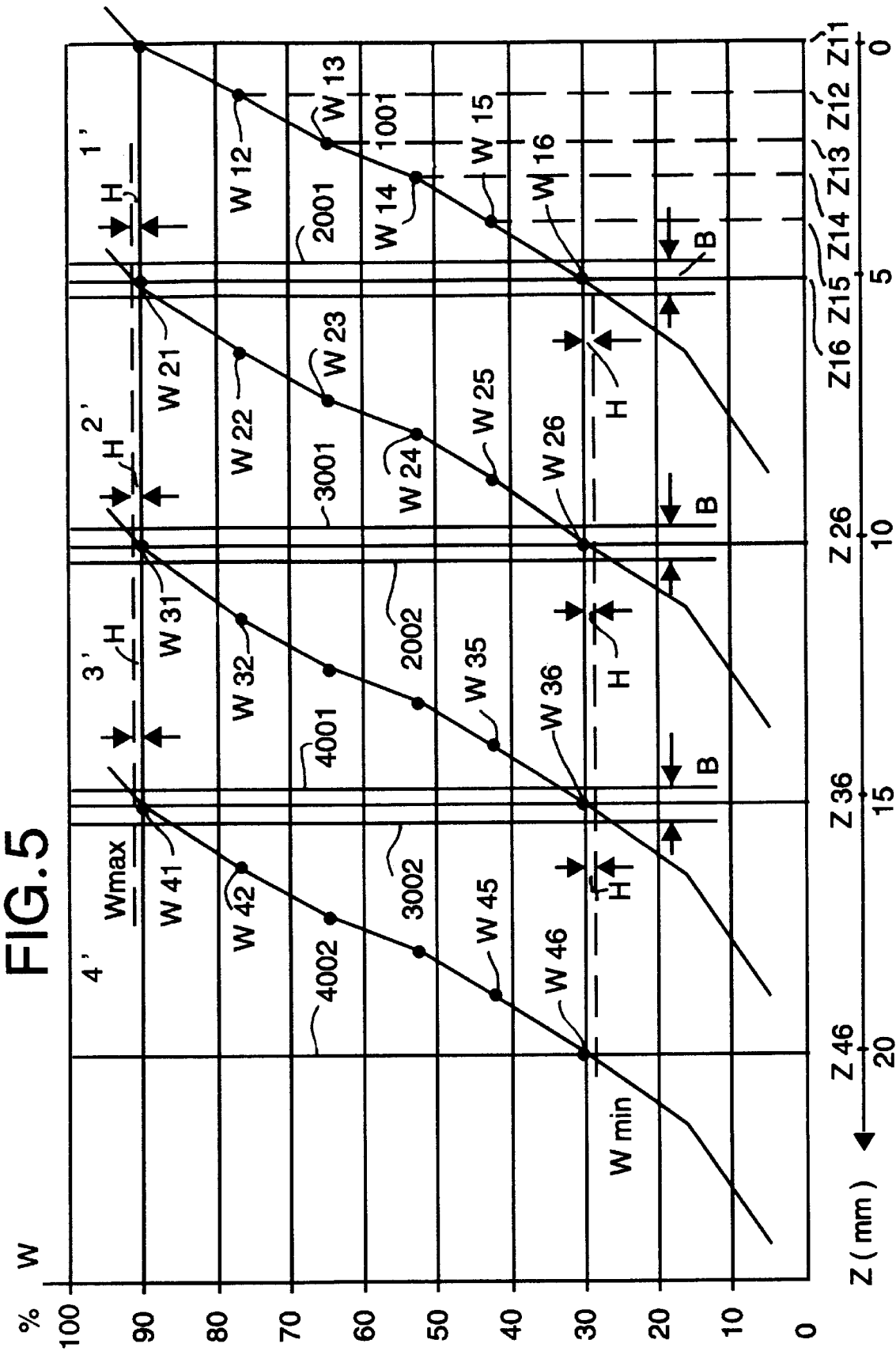
FIG. 5 is a plot of the characteristic illustrating the operation of the edge sensor.

The dependency of the normalized receiver signals on the position of the web edge z and the sensors 1 through 4 which are switched on, has been illustrated in FIG. 5. In FIG. 5 the full value of the receiver signal is represented at 100% W along the abscissor while the depth of penetration of the edge z into the gap 103 has been shown along the ordinate from the right. 100% W represents the maximum normalized receiver signal while $W_{max}$ represents the receiver signal in the empty gap for the sensors 1, 2, 3, 4 across the measuring fields 1', 2', 3', 4', respectively. The value z=0 indicates that the edge of the web has not passed the right hand edge 1001 of the measurement field 1' (compare FIG. 2). Z, as a comparison with FIG. 1 will show, is thus the distance that the web edge 111 may lie within the gap 103 beyond the measurement field edge 1001. The measurement field 1' lies, as a comparison of FIGS. 1 and 5 will show, between z=0 and Z=5 mm. The measurement field 2' extends between Z=5 mm and Z=10 mm. The measurement field 3' extends between Z=10 mm and Z=15 mm and the measurement field 4' extends between Z=15 mm and Z=20 mm. The measurement fields have been represented in FIG. 5 by the respective columns 1', 2', 3', 4'.

Figure 3:
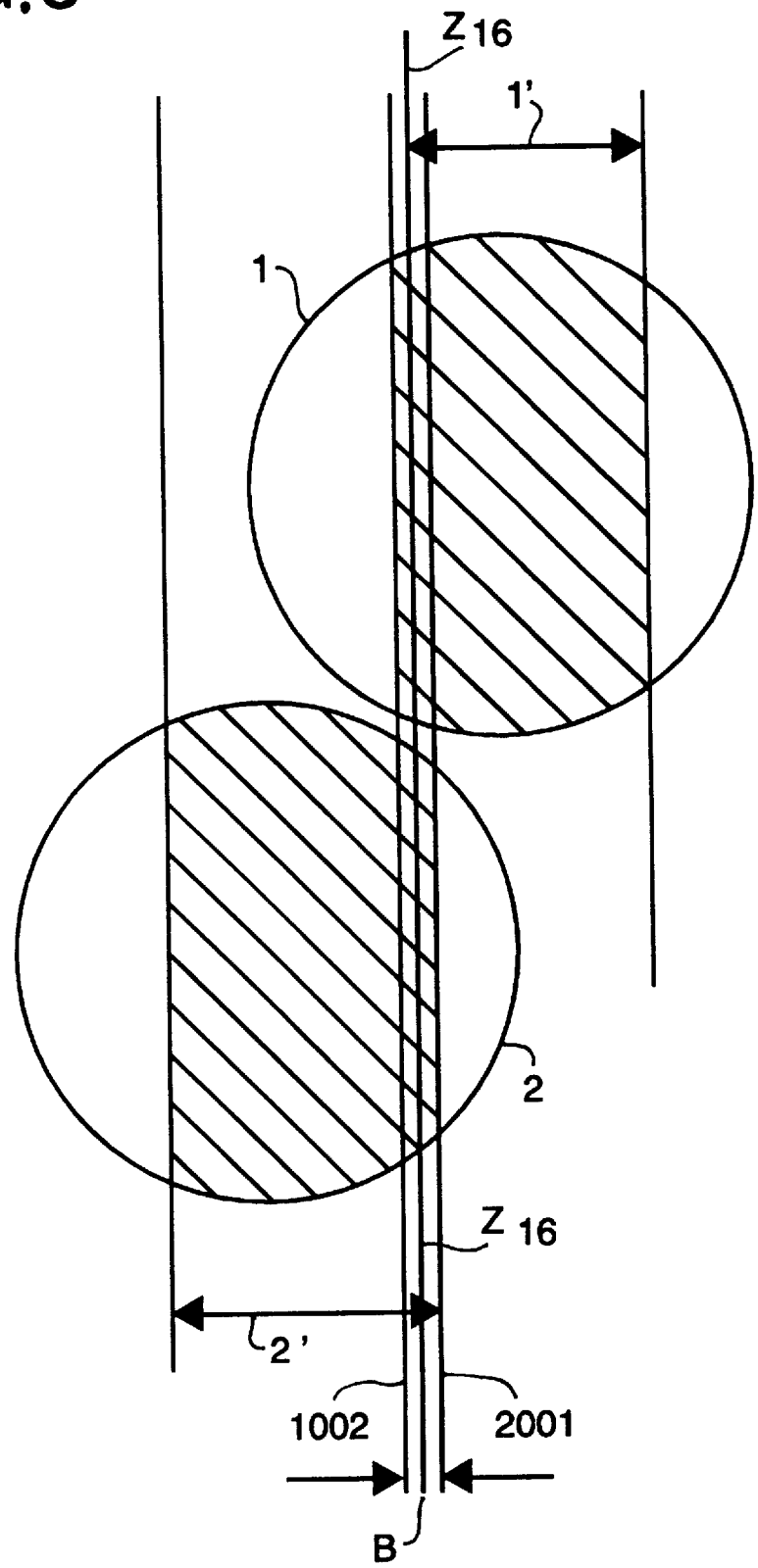
FIG. 3 is a detail of FIG. 2 to still a greater scale.

The measurement fields 1' through 4' of each of the sensors 1 to 4 is thus bounded by two imaginary edge positions 1001, 1002 in the case of the measurement field 1', 2001, 2002 in the case of the measurement field 2', 3001, 3002 in the case of the measurement field 3' and 4001, 4002 in the case of the measurement field 4'. Of course, this means that each of the sensors is usable only within the limits of its measurement field for the measurement of the actual edge position. In the simplified illustration of FIG. 2 the edges of the boundaries 1002, 2001, etc. of neighboring measuring fields 1', 2' or 2', 3' or 3', 4' overlap or coincide. In practice, therefore, the measurement fields overlap slightly as has been shown in the enlarged illustration of FIG. 3 for the example of the fields 1' and 2'. The overlap has been represented in FIG. 5 at B. In the total range of the sensor assembly from edge position 1001 to edge position 4002 of the measurement fields 1' through 4' in the width direction of the web 110 (arrow 112) there is no interruption in the measurement fields. In each right hand position of the edge 1001, 2001, 3001, 4001 for the respective measurement field 1', 2', 3', 4', the receiver signal W has its maximum limiting value $W_{max}$ while in the respective left hand edge position 1002, 2002, 3002, 4002 the output is the minimum limiting value $W_{min}$.

The measurement of the actual position of the web edge 111, therefore, is effected only by a single sensor 1, 2, 3, 4, namely, that in whose measurement field 1', 2', 3', 4', the edge 111 lies between the left and right hand boundaries. As the edge 111 moves from one measurement field to the other, with the switching by multiplexing device 20 the corresponding sensor will be activated. The switchover is controlled with the aid of an up/down or front/back counter represented at 116 in FIG. 6. The counter 116 associates a respective counter state with each of the sensors 1 through 4. With the sensors 1 through 4 switching on the respective measurement fields 1' through 4' in the sequence of the counter states. These counter states correspond to 4 counter outputs 117 via which the counter 116 so controls the electronic switch 20 and its parts 20.1 and 20.2 that in the respective counter state, depending upon the counter output 117 the respective sensor is switched on.

Counter 116 is controlled by a comparator circuit 118 which compares the value W for the actual edge position of the web with the maximum and minimum values $W_{max}$ and $W_{min}$ for the sensors 1 through 4 as they are switched. When a maximum limiting value $W_{max}$ is exceeded or the value of W falls below a minimum value $W_{min}$, the counter 116 is stepped forwardly or rearwardly to the counter state (output 117) so as to bring into play the next sensor 1 through 4 and its measurement field 1' through 4'.

In the calibration data storage 108, calibration values $W_{11}$, $W_{12}$, ... $W_{kn}$ ... $W_{45}$, $W_{46}$ are stored and are represented by corresponding points on the calibration curves for the respective sensors shown in FIG. 5. These points correspond to calibration edge positions $Z_{kn}$ (n=1 to 6) which are equidistantly spaced apart and are located in the measuring fields 1' to 4'. Each measuring field is thus divided into five strips of equal width and, for the sake of simplification, in FIG. 2 only the strips $Z_{22}$, $Z_{23}$, $Z_{24}$, $Z_{25}$, and $Z_{26}$ in measurement field 2' and $Z_{32}$ to $Z_{36}$ for the measurement field 3' are seen. The five strips of the first measurement field 1' have been demarcated at $Z_{1.1}$, $Z_{1.2}$, $Z_{1.3}$, $Z_{1.4}$, $Z_{1.5}$, $Z_{1.6}$.

Each of the calibration edge positions $Z_{16}$ to $Z_{36}$ lies in an overlap region B of two measurement fields 1', 2' or 2', 3' or 3', 4'. For each of these latter calibration edge positions $Z_{16}$, $Z_{26}$ and $Z_{36}$ there are two calibration values of the receiver signal W, namely one from each of the two sensors having the overlapping measurement fields. For example, in the case of the calibration edge position $Z_{16}$, a calibration value of the output $W_{16}$ is obtained for the sensor 1 and a calibration value $W_{21}$ is obtained for the sensor 2. Similarly for the calibration edge position $Z_{26}$, the calibration acoustic output $W_{26}$ is obtained for the sensor 2 and $W_{31}$ for the sensor 3. For the calibration edge position $Z_{36}$, the calibration value $W_{36}$ is obtained for the sensor 3 and $W_{41}$ for the sensor 4. All of these calibration values are obtained in a calibration run in which, instead of a web edge, a standard masking member is stepwise introduced into the gap in the direction of the arrow 112 so that its edge is disposed at the calibration positions $Z_{kn}$ in succession. In each of these positions of the mask the corresponding value $W_{kn}$ of the receiver signal is obtained and stored. This calibration run can be carried out automatically.

The calibration stage 108 also stores a digital calibration value $S_{11}$, $S_{12}$ ... $S_{kn}$ ... $S_{46}$ for the respective sensor output signal S. The calibration values $S_{kn}$ for the calibration edge positions $Z_{kn}$ have the desired dependency on the edge position over any desired range or based upon any desired zero position depending upon whether a linear proportionality of the sensor output signal where the edge position is selected or not.

From the stored calibration values $W_{kn}$, $S_{kn}$, the computer 106 calculates in actual edge position $Z_{kn}$ in dependence upon the value W given by the sensor k upon the value S of the actual sensor output signal as will be described in greater detail subsequently.

It has further been found that each calibration edge position $Z_{k6}$ (k=1–3) which lies within a measurement field overlapping B, is associated with two calibration values for the receiver signal. These each form two calibration values $W_{16}$; $W_{21}$; $W_{26}$; $W_{36}$; $W_{41}$, which, apart from functioning for the calculation of the actual sensor output signal serve as comparison values which compares for each switched on sensor the actual receiver W with the comparison value in the comparator circuit 118. The comparator circuit has a switching hysteresis so that the boundary values $W_{max}$ and $W_{min}$ for the sensor switching each differ by a respective hysteresis interval H from the calibration values and thus such that the maximum limiting value $W_{max}$ is greater by about the hysteresis interval H and the minimal boundary value $W_{min}$ is smaller by a hysteresis H than the respective calibration value $W_{11}$, $W_{21}$, $W_{31}$, $W_{41}$, or $W_{16}$; $W_{26}$; $W_{36}$; $W_{46}$. The comparator circuit 118 has only two comparator units 118.1, 118.2 each with a respective input and a respective output.

Figure 6:
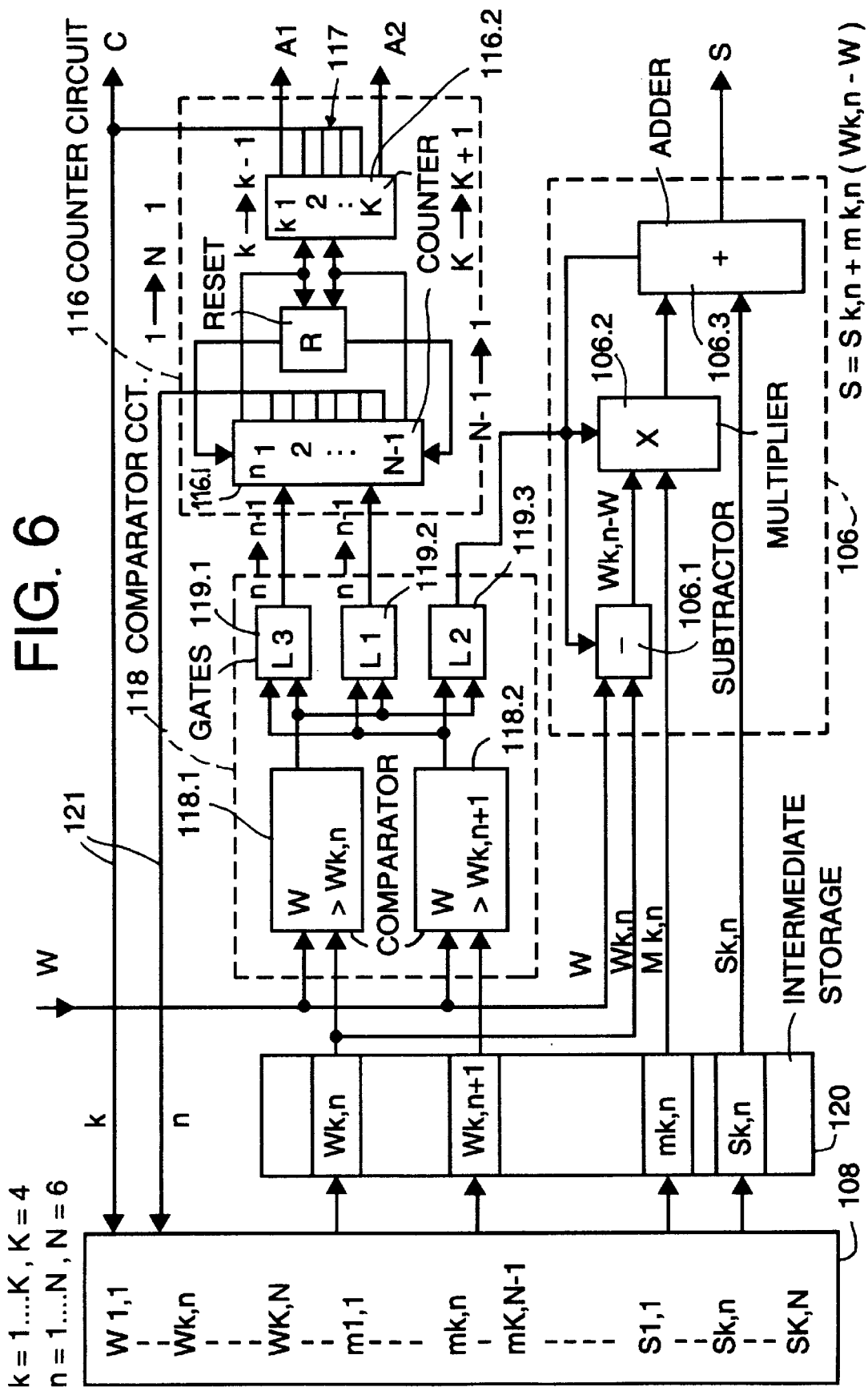
FIG. 6 is a block diagram of the significant parts of the processor of the edge sensor.

As can be seen from FIG. 6, the upper input for each of the comparator units 118.1, 118.2 is supplied with the actual receiver signal W.

In each case the other input can be switched to receive one of the two calibration values $W_{kn}$ and $W_{k(n+1)}$ of the receiving signal from the calibration data storage 108. The respective calibration values $W_{kn}$ and $W_{k(n+1)}$ are associated with respective sequential calibration edge positions $Z_{kn}$, $Z_{k(n+1)}$ were n=1–5 for the respective switched sensors k (k=1–4).

The outputs of the two comparator units 118.1 and 118.2 are combined via gating components 119.1, 119.2 logically for backcounting through the gate 119.1 of the counter 116 and forward counting of the counter 116 through the other gate 119.2 when the actual receiver signal W is greater than the greater or smaller than the lower of the two respective applied calibration values $W_{kn}$, $W_{k(n+1)}$.

A further logic component, namely, the gate 119.3 generates a clearing signal for the counter 106 when the actual receiver signal W is in the interval between the two calibration values $W_{kn}$, $W_{k(n+1)}$ and enables these calibration values to serve for calculation of the actual sensor output signal.

The counter 116, in turn, comprises a forward/back or up-down counter 116.1 directly triggered from the gates 119.1, 119.2 and a further forward/back or up-down counter 116.2 triggered by the up-down counter 116.1.

The first counter 116.1 has a sufficient number of counter states, e.g. 6, to account for the calibration edge positions of each sensor k (k=1–4) which corresponds to a sequence of measuring fields k' (k'=1' to 4'). The second counter 116.2 has a number of states corresponding to the number of sensors, namely, four, and controls via the outputs 117 and line C the switching unit 20 which, in FIG. 4, enables an address coder 20.3 (FIGS. 7A and 7B) via line 50. The first counter 116.1 is automatically reset via the reset R when the counter limit is overstepped in one or the other direction to switch the second counter 116.2 up and back by one counter state. The two counters 116.1, 116.2 with their respective counter states via line 121 and an address decoder not shown in FIG. 6 call out from the calibration data store 108 the calibration values $W_{kn}$, $S_{kn}$ for the switched sensor K associated with the respective calibration edge position $z_{kn}$ for storage in the intermediate memory 120.

If the actual edge position moves out of one of the measurement fields k' into, say, the measurement field (k−1)', the counter 116 switches from sensor k to sensor k−1 as soon as the receiver signal w reaches the value $W_{max}$= $W_{k1}$+H. At this point, the second counter 116.2 is down counted or stepped back by one counter state while the first counter is set from counter state n=1 to the counter state n=5, corresponding to the transition between the calibration value $W_{k1}$ to the calibration value $W_{(k−1)5}$. If the actual edge position then moves from the measurement field (k−1)' back into the measurement field k', there is a sensor switching from k−1 to k when the receiver signal W has fallen to $W_{(k−1)6}$−H. Correspondingly, the first counter 116.1 is reset from counter state n=5 to counter state n=1 corresponding to the transition from calibration value $W_{(k−1)5}$ to calibration value $W_{(k1)}$.

If the actual edge position in the measurement gap 103 oversteps the calibration edge position 211 toward the exterior, the second counter 116.2 will overstep its counting range at the side of the counter state k=1 with the result that, at the output A1 of the counter a range exceeding signal will be generated. A corresponding signal can develop at the output A2 when the actual edge position oversteps inwardly the calibration edge position $Z_{46}$ since the second counter will then overstep at the opposite end its counter state k=4.

In the calibration data storage 108, for each sensor k and each calibration edge position $Z_{kn}$, calibration values $m_{kn}$ are stored for a proportionality factor. These calibration values of the proportionality factor $m_{kn}$ are determined by the relationship $$m_{kn} = \frac{S_k(n+1) - S_{kn}}{W_{k(n+1)} - W_{kn}}$$

This relationship is calculated from the stored calibration values $W_{kn}$, $S_{kn}$ for the received signal and sensor output signal from processor 105.

The value S for the actual sensor output signal is given for an actual edge position z by the value W of the actual receiver signal by the relationship $$S = S_{kn} + m_{kn}*(W - W_{kn}).$$

This calculation is carried out in the computer 106 which has a subtractor 106.1 to which the actual receiver signal W and the calibration value $W_{kn}$ from the intermediate storage 120 are fed. The difference $W_{kn}$-W formed in the subtractor is fed, together with the calibration value $m_{kn}$ from the intermediate storage 120, i.e. the proportionality factor, to the multiplier 106.2, the resulting product being fed to the adder 106.3 together with the calibration value $S_{kn}$ from the intermediate storage 120. The sum is the value of the actual sensor signal S as shown in the previous equation.

The edge positions of the web are thus measured with a measuring cycle over a duration of 1 ms repetitively. The timing diagram of one such cycle has been given in FIG. 8.

At the commencement of the cycle to, initially the transmitter voltage for the active sensor is established, accounting for the duration 122 of about 350 μs. The actual sensor address is established (row III) and the blanking signal is transmitted (row V) to shut off the active sensor receiver.

After the time interval 122, the active sensor transmitter is triggered with the Dirac pulse 128 of a duration of about 5 μs. This transmits an ultrasonic wave pulse of a corresponding duration and the acoustic travel time begins. Until the expected time t1 of arrival of the ultrasonic wave pulse at the sensor receiver, there is a delay interval 127 which depends upon the width of the measurement gap 103 in the head 100 and is adjustable by varying the gap width. Upon the expiration of this delay interval 127, the blanking signal (row V) is terminated and the respective sensor receiver is switched on. Upon the arrival of the ultrasonic wave pulses 123 (row IV) which rapidly decay, a new delay interval 124 of about 80 μs is initiated during which the analog electrical sensor signal is converted into the digital receiver signal. This terminates after a further time interval 125 of about 37 μs so that subsequently by a pulse 126 (row VII) the true sensor output signal is calculated in the computer 106. Upon the conclusion of this calculation of the actual sensor signal, the sensor address for the next measurement cycle is enabled and after a cycle duration of 1 ms, the next measurement cycle is commenced.

Figure 7A:
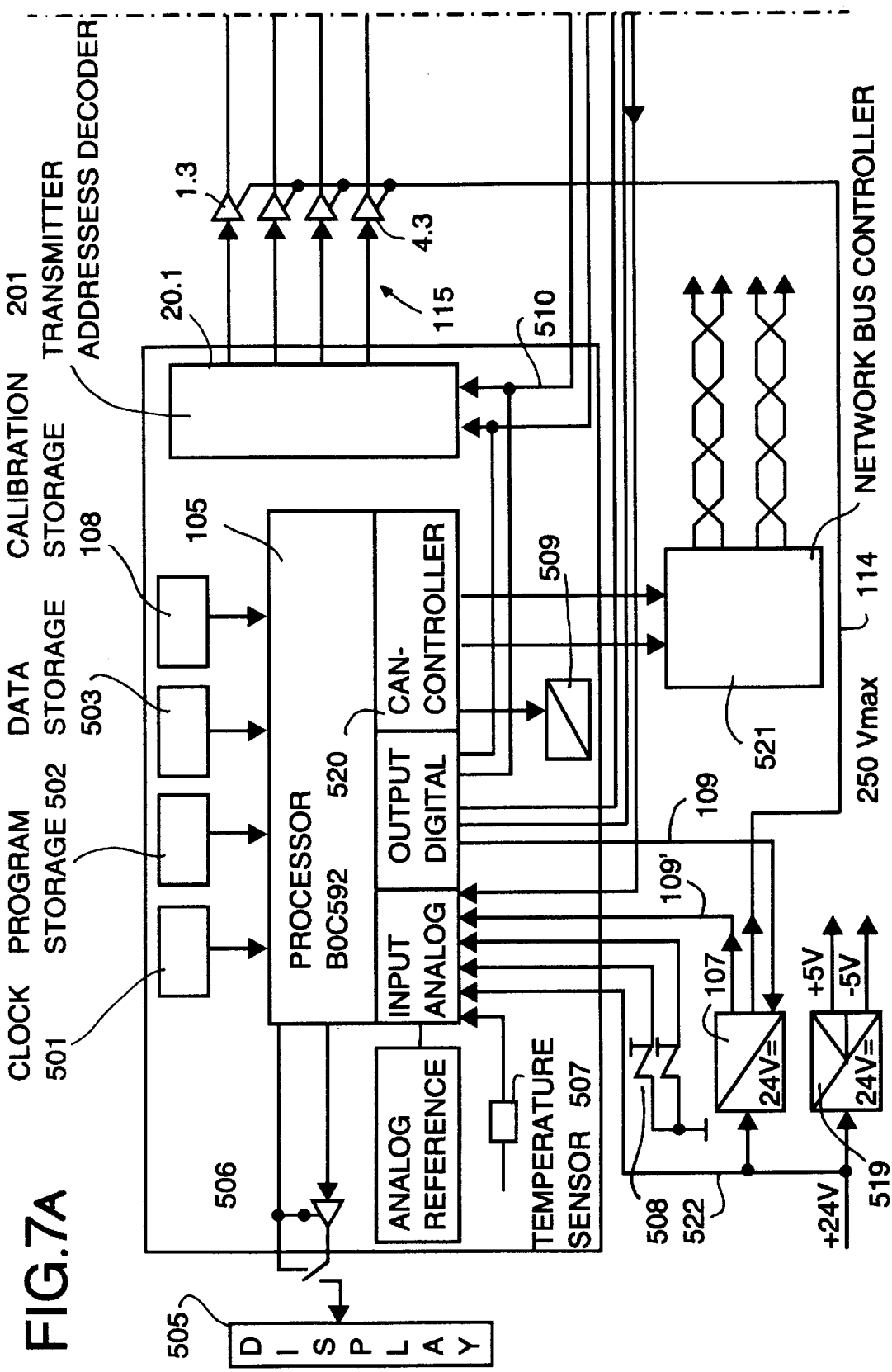
FIGS. 7A and 7B together form is partially a circuit diagram, partially a block diagram and partially a diagrammatic illustration of the interaction of the edge with the measurement fields to illustrate the invention.
Figure 7B:
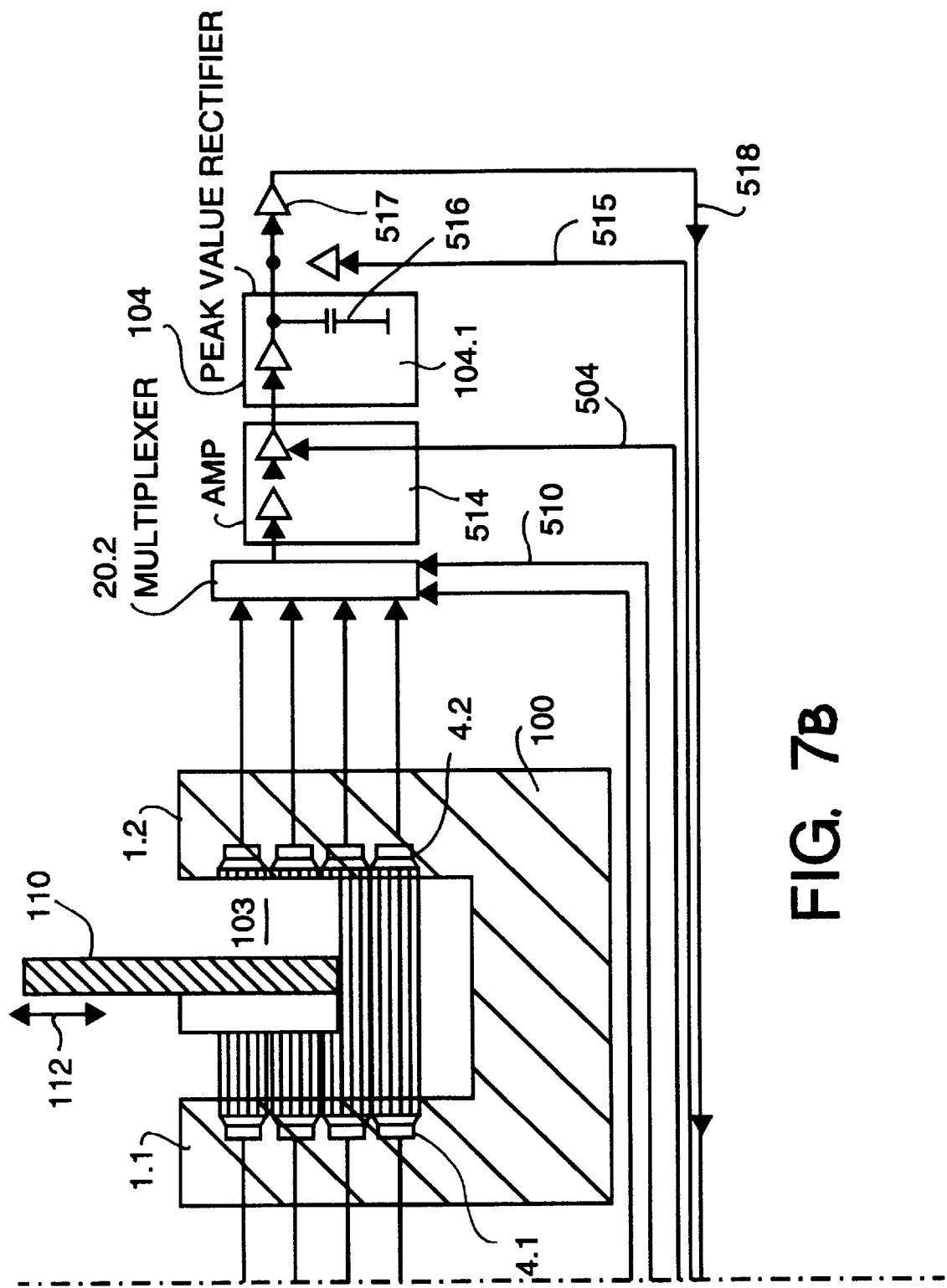

As can be seen from FIGS. 7A and 7B, a reset clock generator 501 produces both the reset signal and the clocking signal at 16 MHz. A program storage 502 is also connected to the processor 105 to supply the controlled program for this processor. The data storage unit 503 connected to the processor 105 contains data temporarily including, for example, a copy of the calibration data stored in the calibration data storage 108. The calibration data storage 108 can be formed as an EEPROM. The EEPROM can store, apart from the calibration values $W_{kn}$, $S_{kn}$, $M_{kn}$, also calibration voltages which are utilized in the calibration operation. The EEPROM can also include any necessary instructions or data required for operation like, for example, device addresses and group addresses. The data is retained even in the case of a voltage supply failure.

A multifunctional display 505 (yellow LED's) indicates the operational state, the device addresses, the group addresses, the measurement range, the actual position of the web edge in the head 100, etc. The LED control 506 can be provided for the brightness of the display and the LED's can be shut down if desired when the unit is used for the detection of the edge of a light-sensitive web. A temperature sensor 507 can continuously measure the operating temperature to compensate for the variation in the sound propagation at the time t1 (FIG. 8) of measurement.

A multifunctional switching system represented at 508 allows the inputting of device and group addresses or the storage and memory of requisite signals or modifications for a particular web (FIGS. 7A and 7B).

A CAN-bus indicator 509 can supply on line the status of the CAN translation. The processor 105 outputs to the sensors which are selected via the lines 510.

The analog multiplexer 20.2 switches on the selected sensor via the respective preamplifier 514 which may be of a two-stage type. The amplification of the preamplifier can be adjusted via the line 504 to match the amplification to the different levels of the receiver signal so that they are independent of the width of the measurement gap 103.

A clear signal supplied on line 515 discharges the condenser 516 of the peak rectifier until the next sound wave signal arrives. An impedance converter 517 with high input and low output impedance limits feedback effects of the processor input on the charging condenser 516 of the peak value rectifier 104.1 which otherwise might affect the analog sensor signal transmitted via line 518 to the processor input.

The setpoint voltage of the voltage generator 107 for the particular sensor in use is adjusted via the control line 109 with a pulse-width modulated signal from the processor 105. The actual voltage is measured via the line 109' and supplied to the processor 105 for voltage level monitoring.

The current supply for the logic components and analog portion of the circuitry has been represented at 519. The processor 105, e.g. an 80C592 can comprise an integrated CAN-bus controller 520 whose input and output signals can be received from and transmitted to an external CAN-bus over a CAN driver 521. The power supply to the processor is monitored via line 522.

We claim:
1. An ultrasonic edge sensor for detecting an edge position of a traveling web, said edge sensor comprising:
   a support;
   at least two ultrasonic sensor units on said support, each of said ultrasonic sensor units being comprised of a transmitter emitting short ultrasonic wave pulses and a receiver responsive to said ultrasonic wave pulses spaced apart across a gap through which an edge of said traveling web can pass, all of said ultrasonic sensor units producing measurement fields across said gap which can be masked by said webs, said receivers having respective receiver outputs dependent upon a degree of masking of the respective measurement field by said web;
   switching means connected to said ultrasonic sensor units and responsive to a degree of penetration of said edge into said gap for switching on the transmitter and the receiver of only a selected one of said ultrasonic sensor units depending upon the degree of penetration of said edge into said gap in a width direction of said web, and for switching over between said sensor units;
   at least one signal converter for forming a digital receiver signal (W) from a respective receiver output of a switched on transmitter and receiver;

a computer connected to said at least one signal converter for producing a sensor output signal (S) representing an edge position of the edge from the digital receiver signal (W) for use in controlling a position of said web, said measurement fields each extending in said width direction between imaginary boundary edge positions at which the receiver signal (W) is a maximum at one side of the respective field and at which the receiver signal (W) is a minimum at the opposite side of the measurement field, said measurement fields being arrayed in said direction without a gap between them;

a forward/backward counter having a number of counter states equal to the number of said sensor units, said counter being connected to said switching means to shift from counter state to counter state and switch over from sensor unit to sensor unit successively as said counter states change and as said edge of the web changes position in said gap;

a comparator circuit connected to said signal converter for comparing a receiver signal (W) for an actual position of said edge with the maximum ($W_{max}$) and the minimum ($W_{min}$) of the respective sensor unit and stepping said counter forward and back selectively upon said receiver signal (W) exceeding said maximum ($W_{max}$) and said receiver signal (W) falling below said minimum ($W_{min}$), thereby turning on the transmitter and receiver of a respective one of the sensor units having an adjacent measurement field; and a calibration data memory storing for receiver signals (W) of the respective switched-on transmitter and receiver and for respective sensor output signals (S) calibration values ($W_{kn}$, $S_{kn}$) associated with respective calibration edge positions ($Z_{kn}$) distributed over the measurement fields of all of said ultrasonic sensor units, the computer being provided with means for calculating an actual edge position (Z) from the sensor output signal (S) for a receiver signal (W) of the switched on sensor unit from the stored calibration values ($W_{kn}$, $S_{kn}$) thereof.

2. The ultrasonic edge sensor defined in claim 1 wherein said measurement fields are provided in at least one row with mutually adjoining measurement fields overlapping in pairs.

3. The ultrasonic edge sensor defined in claim 2 wherein said calibration edge positions correspond to the respective imaginary boundary edge positions.

4. The ultrasonic edge sensor defined in claim 2 wherein for each overlap of pairs of said measurement fields there is only a single calibration edge position ($Z_{16}$, $Z_{26}$, $Z_{36}$) assigned to two calibration values ($W_{kn}$) of the respective pair, the said two calibration values being compared in said comparator circuit with the receiver signal (W) of the turned on sensor unit, the comparator circuit having a hysteresis such that for switchover of the sensor units the maximum ($W_{max}$) and the minimum ($W_{min}$) is greater and less than the respective calibration values by the hysteresis interval (H).

5. The ultrasonic edge sensor defined in claim 1 wherein the comparator circuit comprises only two comparators each having two inputs and one output, one of the inputs of each comparator receiving the receiver signal (W), the other input of each comparator receiving a respective one of said calibration values ($W_{kn}$, $W_{k(n+1)}$) of two successive measurement fields, the outputs of said comparators being fed to logic elements connected to said counter for advancing and backstepping the counter when said receiving signal (W) is greater than the larger or smaller than the smaller of said calibration values ($W_{kn}$, $W_{k(n+1)}$).

6. The ultrasonic edge sensor defined in claim 5, further comprising another logic element combining outputs from said comparators and generating in said computer a signal when said receiver signal (W) lies in an interval between the respective calibration values ($W_{kn}$, $W_{k(n+1)}$).

7. The ultrasonic edge sensor defined in claim 5 wherein said counter includes a first up-down counter directly triggered by said logic elements and a second up-down counter triggered by the first up-down counter, said first up-down counter having a number of counter states corresponding to the number of calibration edge positions for each sensor and the second up-down counter having a number of counter states corresponding to the number of sensor units, whereby said first up-down counter is automatically reset upon overstepping the number of counter states thereof and a second counter being stepped upon the resetting of said first counter, said calibration data memory including an address coder responsive to the counter states of said counters.

8. The ultrasonic edge sensor defined in claim 7 wherein each sensor unit has the same number of calibration edge positions assigned thereto.

9. The ultrasonic edge sensor defined in claim 1 wherein said calibration data memory source for each sensor (k) and each calibration edge position ($z_{kn}$) calibration values ($m_{kn}$) for a proportionality factor associated with the calibration values ($W_{kn}$, $S_{kn}$) corresponding to the calibration edge position ($z_{kn}$) of the receiver signal and the sensor output signal, respectively, and for an actual edge position (z) the value (S) of the sensor output is calculated from the value (W) of the receiver signal in accordance with the equations $$S = S_{kn} + m_{kn} * (W - W_{kn}).$$

$$m_{kn} = \frac{S_k(n+1) - S_{kn}}{W_{k(n+1)} - W_{kn}}$$

wherein $W_{kn}$, $S_{kn}$, $W_{k(n+1)}$, $S_{k(n+1)}$ are the receiver and sensor output signals for the nth and n+1th calibration edge positions for the kth sensor and $m_{kn}$ is the proportionality factor relating the calibration values $W_{kn}$, $S_{kn}$.

10. The ultrasonic edge sensor defined in claim 9 wherein the computer comprises a subtracter forming the difference ($W_{kn}-W$), a multiplier forming the product $m_{kn}\cdot(W_{kn}-W)$, and the summer for forming the summation $S_{kn}+m_{kn}\cdot(W_{kn}-W)$.

11. The ultrasonic edge sensor defined in claim 1, further comprising at least one voltage generator for said transmitters for applying respective calibration voltages to the transmitters of said sensor units so that, in the absence of an object in the respective measurement field, the same receiver signal magnitude is generated at each of said receiver.

* * * * *